United States Patent [19]
Nishino et al.

[11] Patent Number: 5,429,180
[45] Date of Patent: Jul. 4, 1995

[54] PERFUME GENERATING DEVICE

[75] Inventors: Tomohide Nishino; Toshiaki Fukuta; Yukiya Sassa, all of Nagoya, Japan

[73] Assignee: Nippondenso Co., Ltd., Kariya, Japan

[21] Appl. No.: 130,506

[22] Filed: Oct. 1, 1993

[30] Foreign Application Priority Data

Oct. 2, 1992 [JP] Japan ................. 4-068895 U
Oct. 15, 1992 [JP] Japan ................. 4-277075

[51] Int. Cl.⁶ ............................................. F28D 15/00
[52] U.S. Cl. ............................................ 165/41; 62/78; 422/124
[58] Field of Search .............. 165/41, 51, 53; 62/78; 422/120, 122, 123, 124, 4

[56] References Cited

U.S. PATENT DOCUMENTS

| | | | |
|---|---|---|---|
| 4,948,567 | 8/1990 | Atarashiya | 422/4 |
| 5,078,971 | 1/1992 | Matuda | 422/124 |
| 5,267,608 | 12/1993 | Coffinberry | 165/41 |
| 5,323,624 | 6/1994 | Schwalm | 62/78 |
| 5,327,739 | 7/1994 | Ingersoll | 62/78 |
| 5,347,820 | 9/1994 | Gweon | 62/78 |
| 5,351,747 | 10/1994 | Koeppi | 165/41 |

FOREIGN PATENT DOCUMENTS

| | | |
|---|---|---|
| 58-81817 | 5/1983 | Japan . |
| 260821 | 3/1990 | Japan . |
| 2225125 | 9/1990 | Japan . |
| 4170964 | 6/1992 | Japan . |

Primary Examiner—Ira S. Lazarus
Assistant Examiner—Daniel J. O'Connor
Attorney, Agent, or Firm—Cushman, Darby & Cushman

[57] ABSTRACT

A perfume generating device for preventing a reduction in the level of a consciousness by a supply of relaxing-type aromatic agent, and for preventing a reduction in concentration. Different containers for relaxing-type and refreshing-type aromatic agents and valves for selecting one of the agents are provided on a perfume supply conduit. Upon the selection of the relaxing-type aromatic agent, a repetition of cycles are executed such that, after each three cycles of a relaxing-type aromatic agent, a single supply of refreshing-type aromatic agent or stoppage of the supply of the relaxing-type aromatic agent is performed.

12 Claims, 10 Drawing Sheets

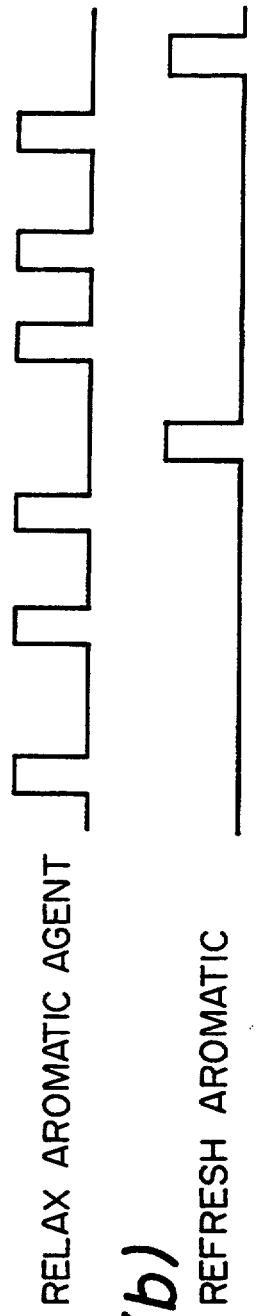
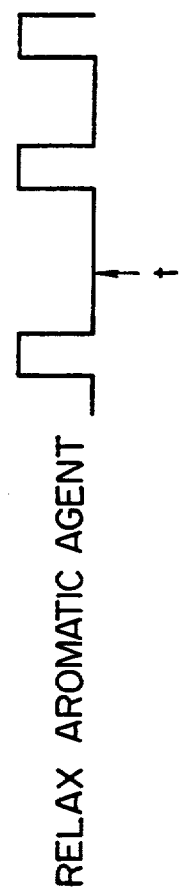

PERFUME GENERATING DEVICE

BACKGROUND

1. Field of the Invention

The present invention relates to an apparatus for generating an aroma by volatilizing an aromatic agent or agents.

2. Description of Related Art

Various types of apparatus for generating aroma in a chamber by using one or more volatilizable aromatic agent have been proposed. When such a volatilizable aromatic used in these types of aroma generating apparatus is subjected to volatilization, which takes place naturally, the density of the aroma increases as the time lapses. Contrary to this, a substantial reduction in sensitivity to an aroma will occur upon a lapse of time. A perfume generating device has therefore been proposed where the supply of the aromatic agent is controlled in accordance with time, thereby maintaining a desirable aromatic circumstance in a space for relatively prolonged time. See Japanese Un-Examined Patent Publication No. 2-60821 and Japanese Un-Examined Patent Publication No. 2-225125.

In the perfume generating device in the above mentioned prior arts, it is proposed to use a plurality of different aromatic agents, one of which is usually selected when used. When it is desired, two or more kinds of aromatic agents are mixed for use. In case where such different aromatic agents are used, a unified control of the device has been employed irrespective of the different aromatic natures of the agents. When an aromatic agent, as selected by a user, provides an aroma for providing a relaxing effect, the prolonged use of such aroma can cause the concentration level to fall. Namely, a continuous supply of the aroma providing a relaxing effect in a vehicle or a factory may sometimes be unsuitable from the view point of safety.

In an Un-Examined Japanese Patent Publication No. 4-170964, a three way branched box is provided, which is provided with cassettes for different aromatic agents. A pipe is provided for connecting a downstream end of an air conditioning duct with the three way branched box. Valve units are provided for obtaining a connection of the pipe with the cassettes of different aromatic agents. The valve units controls the amount of the respective odor components, so that a desired rate of mixing of the odor agents supplied to the air conditioning duct is obtained.

In the Japanese Un-Examined Patent Publication No. 58-81817, a container for storing a deodorant agent is arranged outside the air conditioning duct of an air conditioning system for a vehicle. The deodorant container is connected to the air conditioning duct via two pipes. The dynamic pressure in the air conditioning duct, generated by the flow of the air in the duct, is used to generate a flow of the deodorant agent from the container into the air conditioning duct.

In the Un-Examined Japanese Patent Publication No. 4-170964, the odor supply port at the end of the pipe is opened to the air conditioning duct at a location which is downstream from a front outlet damper for selectively opening or closing the front outlet (vent outlet) opened to the cabin for creating a flow of warm air toward lower portion of the cabin during low-level-mode operation. The damper closes the vent outlet at modes other than the low-level mode. In other word, the prior art is defective that a supply of the odor to the cabin is obtained only when the low level mode is selected.

In the Japanese Un-Examined Patent Publication No. 58-81817, the deodorant supply opening at the end of the pipe is opened to the air conditioning duct at a location upstream from a heater core. As a result, an absorption of the deodorant takes place at the heater core, causing the amount of the deodorant supplied to the cabin to be decreased, causing the deodorization efficiency to fall.

SUMMARY OF THE INVENTION

An object of the present invention is to provide a perfume generating apparatus capable of preventing a fall in the level of concentration due to a continuous supply of a relaxing-type aromatic agent.

Another object of the present invention is to provide a perfume generating device for a vehicle capable of obtaining a desired amount of the aromatic agent in the cabin irrespective of the air conditioning mode selected.

According to a first aspect of the invention, a perfume generating apparatus is provided, comprising:
(a) a first container for storing a volatile, relaxing type aromatic agent capable of giving a relaxing effect.
(b) a second container for storing a volatile, refreshing type aromatic agent capable of giving a refreshing effect.
(c) first means, responsive to an electric signal, for selectively opening the first container;
(d) second means, responsive to an electric signal, for selectively opening the second container;
(e) means for issuing an instruction for commencing a supply of the aromatic agents, and;
(f) means for issuing electric signals to the first and second means for obtaining repetitions of cycles of supply of the relaxing type aromatic agent for a first predetermined period which is followed by supply of the refreshing type aromatic agent for a second predetermined period, when instructed.

According to a second aspect of the invention, a perfume generating apparatus is provided, comprising:
(a) a container for storing a volatile, relaxing type aromatic agent capable of giving a relaxing effect;
(b) first means, responsive to an electric signal, for selectively opening said container;
(c) means for issuing an instruction to commence the supply of the aromatic agents, and;
(d) means for issuing electric signals supplied to the container opening means for obtaining a repetition of cycles of supply of the relaxing type aromatic agent for a first predetermined period, which are followed by a stoppage of supply of the relaxing type aromatic agent for a second predetermined period, when instructed.

BRIEF DESCRIPTION OF ATTACHED DRAWINGS

FIG. 8A and 8B is a timing chart illustrating how the supply operation of the aromatic agents is done in the first embodiment.

FIG. 10 is a timing chart illustrating how the supply operation of the aromatic agents is performed in the second embodiment.

DESCRIPTION OF PREFERRED EMBODIMENTS

Figure 1:
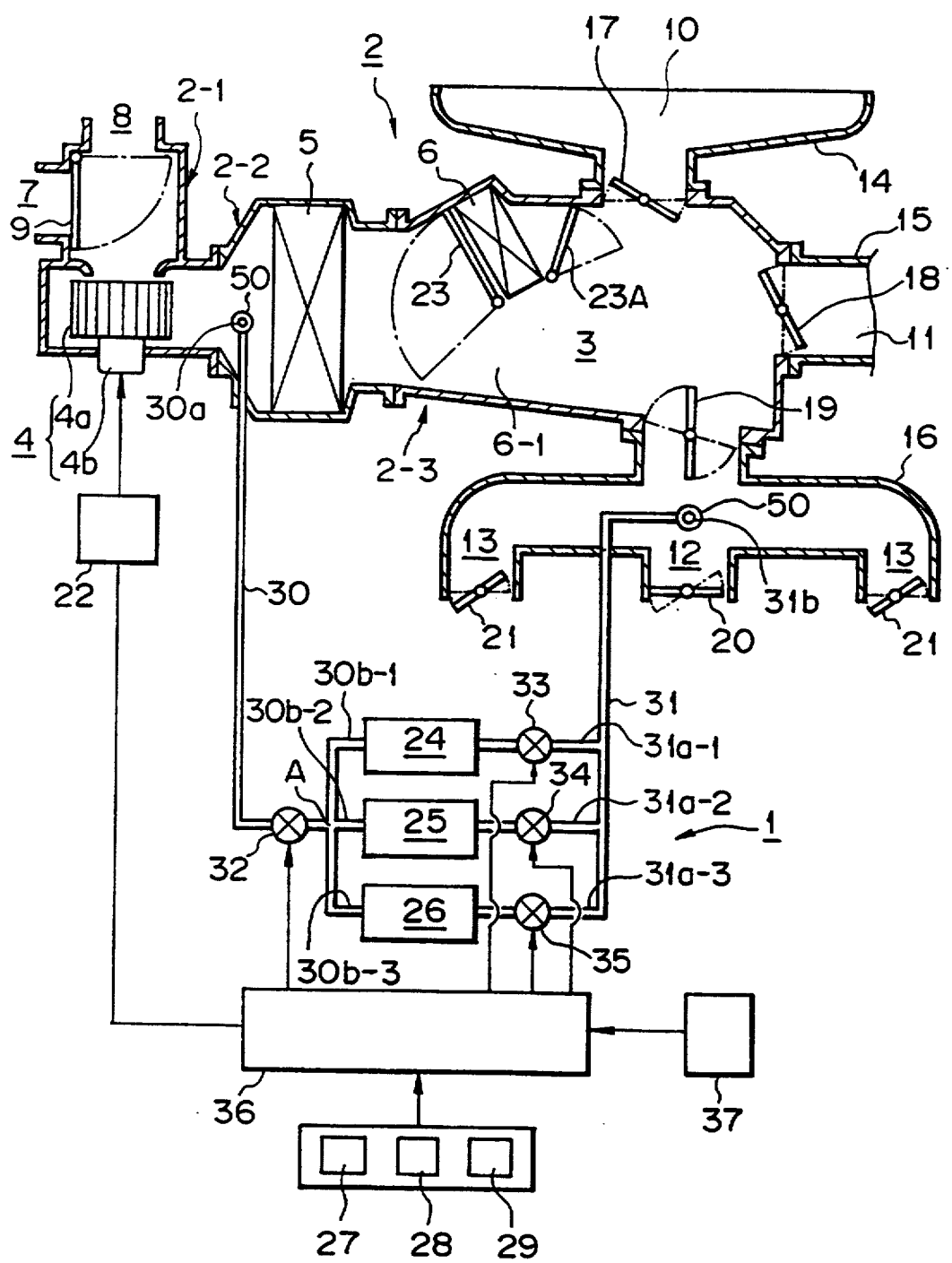
FIG. 1 is a schematic, general view of an air conditioning device for a vehicle provided with a perfume generating device according to the present invention.

Referring to FIG. 1, showing a general view of an air conditioning system 2 for an automobile provided with a perfume generating device according to the invention, the air conditioning system 2 is provided with an air duct 3 for creating a flow of air for air conditioning introduced into a cabin of an automobile having an internal combustion engine. Arranged in the duct 3 is a blower 4 for obtaining a flow of the air in the duct 3, an evaporator 5 for a refrigerating medium, and a heater core 6 arranged in the duct 3 at a location downstream from the evaporator 5. The evaporator 5 is located in a refrigerating circuit, which is, in a known manner, constructed by, in addition to the evaporator 5, a compressor (not shown), a condenser (not shown) for receiving the refrigerant from the compressor, and a expansion valve arranged between the condenser and the evaporator for reducing the pressure of the refrigerant. The heater core 6 is connected to a engine water cooling circuit (not shown) so that the engine cooling water at a high temperature is taken from the engine water cooling line.

As shown in FIG. 1, the air conditioning system 2 includes a blower unit 2-1 for housing the blower 4, a cooling unit 2-2 for housing the refrigerant evaporator 5 and the heater unit 2-3 for storing the heater core 5.

The blower unit 2-1 is provided with an inlet 7 for introduction of air from inside the cabin and an inlet 8 for introduction of air from outside the cabin. The blower unit 2-1 is further provided with a switching damper 9, which is moved between a position as shown by a solid line, where the outside air inlet 8 is opened for introduction of the outside air and a position as shown by a phantom line, where the inside air inlet 7 is opened for introduction of the inside air.

The blower 4 is constructed by a centrifugal fan 4a and an electric motor 4b connected to the fan 4a for imparting the rotational movement thereto. The rotational speed of the fan 4a is varied in accordance with the voltage supplied to the electric motor 4b. The fan motor 4b is supplied by a drive circuit 22 which is operated by a control circuit 36.

As shown in FIG. 1, the heater core 6 is arranged inside the duct 3, so that a passageway 6-1 by-passing the heater core 6 is created. A first air mix damper 23 is arranged on the upstream side of the heater core 6, and is moved between a position as shown by a solid line to open the by-pass passageway 6-1, allowing the air flow to pass through the by-pass passageway 6-1 and for preventing the flow of the air into the heater core 6 and a position as shown by a phantom line to close the by-pass passageway 6-1, allowing the air flow to pass through the heater core 6 and for preventing the flow of the air into the by-pass passageway 6-1. At an intermediate position, the ratio of the amount of the air passed through the heater core 6 to the amount of the air passed thorough the by-pass passageway 6-1 is controlled in accordance with the degree of the opening of the valve 23, for controlling the temperature of the air when the air from the heater core 6 and the air from the by-pass passageway 6-1 are mixed. The second air-mix damper 23A is arranged at the outlet side of the heater core 6, and is moved between a position as shown by a solid line and a position as shown by a phantom line.

The heating unit 2-3 is connected to a plurality of outlet duct including a defroster duct 14, a lower duct (a foot outlet duct) 15, and an upper duct (a vent or face duct) 16, which respectively have the defroster outlet 10, lower outlet 11 and, upper, center outlets 12 and upper side outlets 13. Arranged at the defroster duct 14, the lower duct 15, and the upper duct 16 are various control dampers, such as a defroster control damper 17, a lower outlet control damper 18 and upper outlet control damper 19, which are operated in accordance with selected operating modes. Furthermore, a upper, center damper 20 and upper, side dampers 21 are provided for controlling the upper, center outlet 12 and the side, upper outlets 13, respectively. In FIG. 1 the lower duct 15 is shown at a higher location while the upper outlet duct 16 is shown in a lower location, for the sake of the simplicity of a drawing. However, the upper duct 16 is opened to a vertical location in a cabin corresponding to an upper part of a driver or a passenger, while the lower duct 15 is opened to a vertical location corresponding to a lower part of a driver or passenger in the cabin.

Figure 2:
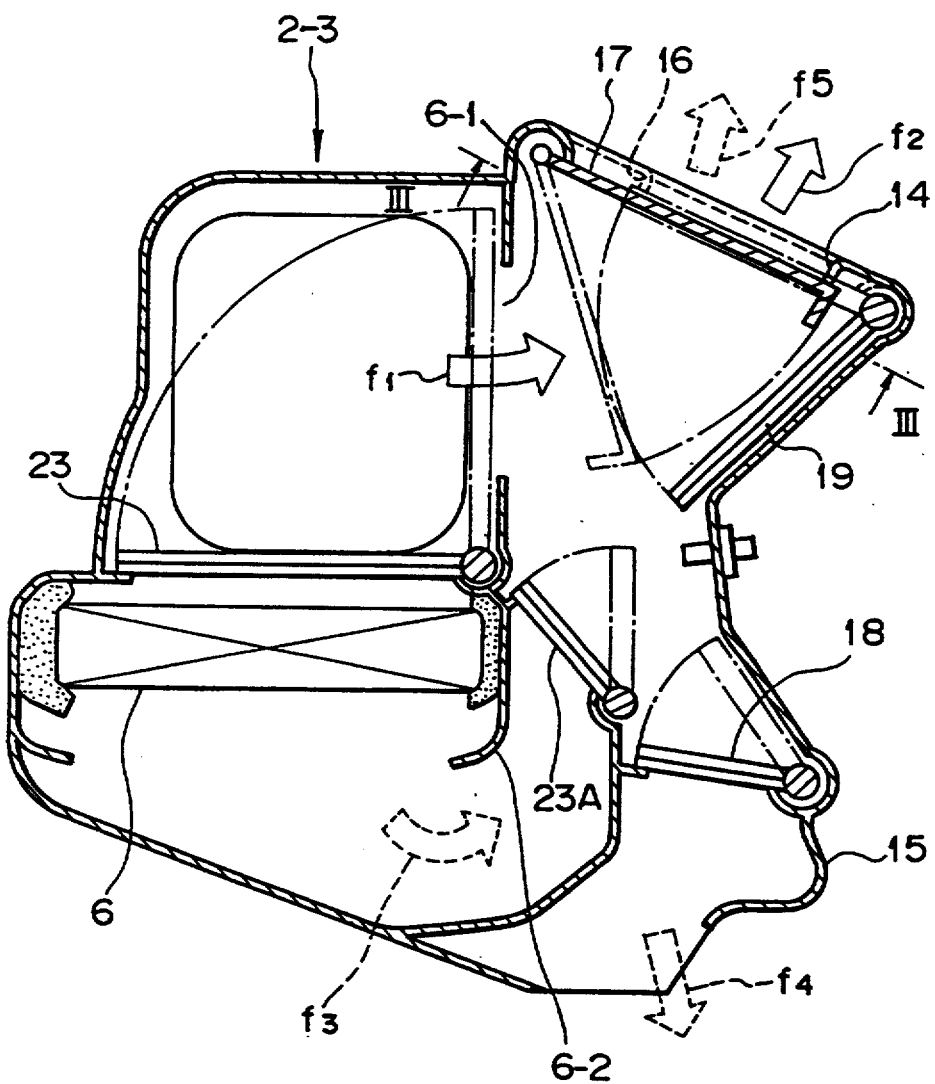
FIG. 2 is a detail of a heater unit of the air conditioning device in FIG. 1.

In FIG. 2, showing a detailed construction of a heating unit 2-3, the solid arrow as outlined shows the flow of air (low temperature air) during a cooling mode, so that a low temperature air flow from the upper outlets 12 and 13 (FIG. 1) is obtained. During the cooling mode, the air-mix damper 23 and 23A, and the outlet-control dampers 17, 18 and 19 are in the positions shown by solid lines, respectively. Namely, all of the air, after passing the evaporator 5 (FIG. 1) passes through the by-pass passageway 6-1 as shown by the arrow $f_1$, and is directed to the upper outlet duct 16 as shown by the arrow $f_2$, due to the fact that the upper outlet control damper 19 is at a position to open the upper outlet duct 16, while the first air mix damper 23 is in the position to close the opening to the heater core 6, the second air mix damper 23A is in a position to close a duct 6-2 from the heater core 6, and the lower outlet control damper 18 closes the lower outlet duct 15.

During a heating mode or defrosting mode, a flow of hot air from the lower outlet 11 (FIG. 1) as shown by dotted arrows as outlined is obtained. Namely, the air mix dampers 23 and 23A are switched to position as shown by dotted lines, so that the all of the air, after passing the evaporator 5, is directed to the heater core 6 and the duct 6-2 as shown by the arrow $f_3$. In the heating mode, the lower outlet control damper 18 opens the lower outlet duct 15, so that an air flow from the lower outlet 11 is obtained as shown by the arrow $f_4$. In the defrosting mode, the defroster control valve 17 opens the defroster duct 14, so that an air flow from the defroster outlet 10 is obtained as shown by the dotted arrow $f_5$.

Figure 3:
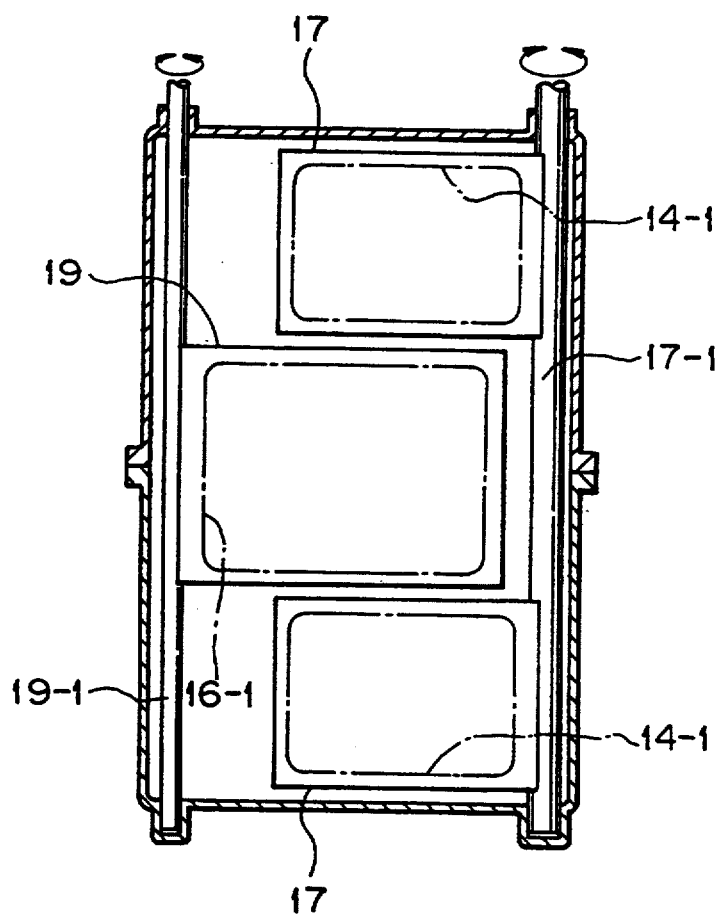
FIG. 3 is a view taken along line III—III in FIG. 2.

As shown in FIG. 3, a pair of openings 14-1 to the defroster ducts 14 are arranged on both sides of an opening 16-1 to the upper duct 16. The valves 17 may be constructed as a flap valve, having a drive shaft 17-1 to which the valves 17 are connected on one hand and an actuator motor (not shown) is connected for imparting a rotational movement thereto. Similarly, the valve 19 may be constructed as a flap valve having a drive shaft 19-1.

As shown in FIG. 1, a reference numeral 1 denotes a perfume generating device which is arranged outside the air conditioning duct 3. The device 1 includes three cassettes or containers 24, 25 and 26 for storing volatilizable aromatic agents of different perfumes, respectively, switches 27, 28 and 29 operated by a passenger for selecting a desired aromatic or deodorant, and a control means for supplying the odor agent(s) selected by the switches 27, 28 and 29 to the air conditioning duct 3. The control means includes: an upstream pipe 30 having an upstream end 30a connected to the air conditioning duct 3 at a location between the blower 4 and the evaporator 5, and branched, parallel downstream ends 30b-1, 30b-2 and 30b-3 connected to the cassettes 24, 25 and 26, respectively; a downstream pipe 31 having branched, parallel upstream ends 31a-1, 31a-2 and 31a-3 connected to the cassettes 24, 25 and 26, respectively; a downstream end 31b connected to the upper outlet duct 16 at a location downstream from the damper 19 and upstream from the outlets 12 and 13; an electromagnetic valve 32 on the upstream pipe 30 upstream from the branched portions 30a-1, 30a-2 and 30a-3, and; electromagnetic valves 33, 34 and 35 on the branched portions 31a-1, 31a-2 and 31a-3, respectively.

The aromatic agents as used are, for example, a relaxing type aromatic agent, such as Eremine, Forest or Lemon et. al., that provides a relaxing effect, and a refreshing type aromatic agent, such as Mint, Floral or Musk, that provides a refreshing effect, which are stored in the cassettes 24 and 25, respectively. A deodorant is stored in the cassette 26.

Figure 4:
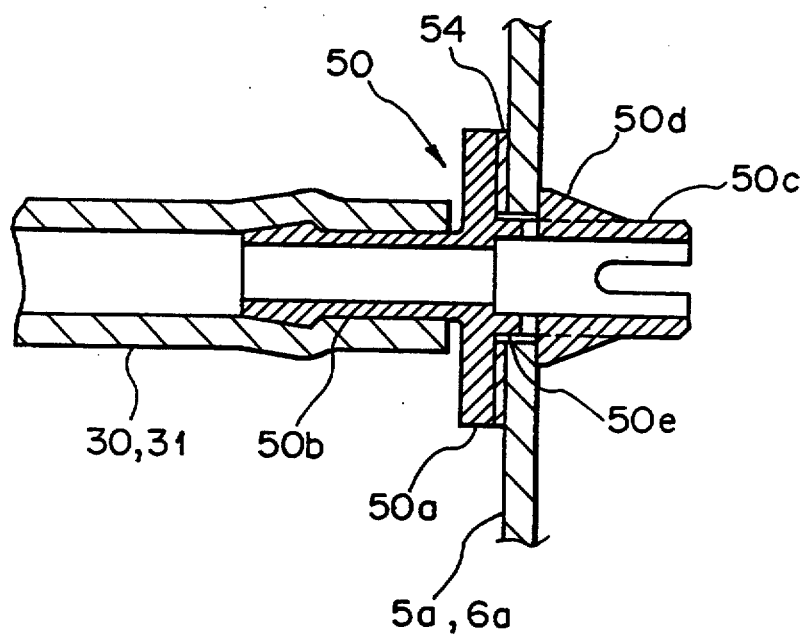
FIG. 4 is a cross sectional view of a joint pipe in FIG. 1.

The upstream and downstream pipes 30 and 31 are made from rubber, and are connected, via joint pipes 50, to the cooling unit 2-2 and the upper outlet duct 16, respectively. Each of the joint pipes 50 has, as shown in FIG. 4, a flange portion 50a at its one end, which is fixedly connected to an outer wall 5a or 6a of the unit 2-2 or 16 by means of adhesive sheet 54. Furthermore, each joint pipe 50 has a first tubular portion 50b at its one side adjacent the tube 30 or 31, to which tubular portion 50b the rubber pipe 30 or 31 are fitted, and has a second tubular portion 50c at the other side of the flange 50a remote from the first tube portion 50b. The second tubular portion 50c has circumferentially spaced, radially extending finger portions 50d which are forwardly tapered. An annular groove 50e is formed between the flange portion 50a and the finger portions 50d. When a connection of the pipe 30 and 31 is made, the walls 5a or 6a are moved over the finger portion 50d, which causes the finger portions 50d to be radially deformed, which causes the walls 5a or 6a to clear the finger portions 50d, causing the wall 5a or 6a to be snap-fitted to the groove 50e, which prevent the joint pipe 50 from being easily disengaged from the unit 2-2 or 16.

Figure 5:
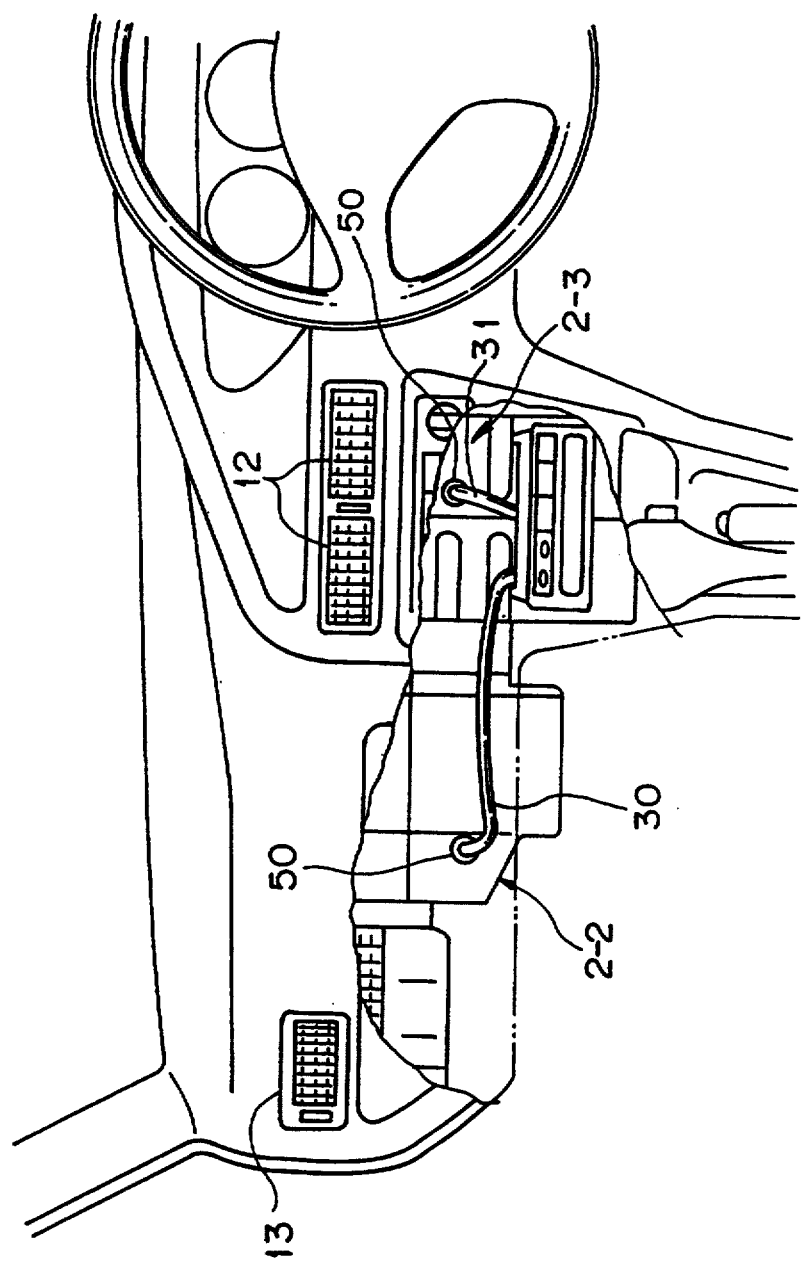
FIG. 5 is a perspective view of a front portion of a cabin of a vehicle provided with the air conditioning system according to the present invention.

It should be noted that the location where the joint pipes 50 are connected to the cooling unit 2-2 and the upper outlet duct 16, respectively are determined by considering the ease in arranging the upstream pipe 30 and the downstream pipe 31 with respect to the cooling unit 2-2 and the heater unit 2-3, respectively. For example, as shown in FIG. 5, the joint pipe 50 for connecting the upstream pipe 30 to the cooling unit 2-2 is located on a side wall of the cooling unit 2-2 facing the cabin near the passenger's seat, and the joint pipe 50 for connecting the downstream pipe 31 with the upper duct 16 extends up to the duct 16 along a side wall of the unit 2-3 facing the cabin, which wall is usually covered by a panel on which an audio unit or a control switches for an air conditional are furnished.

The selection switch 27 is for selection of the relaxing-type aromatic agent. When the switch 27 is ON, a control circuit 36 issues a signal for energize the electromagnetic valves 32 and 33, which connects the upstream pipe 30 to the downstream pipe 31 via the branched portions 30b-1 and 31a-1, which allows the relaxing type aromatic agent to be supplied from the cassette 24.

The selection switch 28 is for selection of the refreshing type aromatic agent. When the switch 28 is ON, a control circuit 36 issues a signal to energize the electromagnetic valves 32 and 34, which connects the upstream pipe 30 to the downstream pipe 31 via the branched portions 30b-2 and 31a-2, which allows the refresh type aromatic agent to be supplied from the cassette 25.

The selection switch 29 is for selection of the deodorant. When the switch 29 is ON, a control circuit 36 issues a signal to energizing the electromagnetic valves 32 and 35, which allows the upstream pipe 30 to be connected to the downstream pipe 31 via the branched portions 30b-3 and 31a-3, which allows the deodorant from the cassette 26 to be supplied.

Connected to the control circuit 36 is a 1/f type random pulse generating circuit 37, which generates random pulses having output power spectrum which is inversely proportional to the frequency. When one of the switches 27 to 29 is made ON, the random pulses from the circuit 37 cause the control circuit 36 to randomly and pulsatively operate a selected combination of the electromagnetic valves 32 to 35. Furthermore, upon a selection of the refreshing-type aromatic agent, the control circuit 36 operates the electromagnetic valves 32 to 35 under a preset pattern as shown in FIG. 8.

Figure 6:
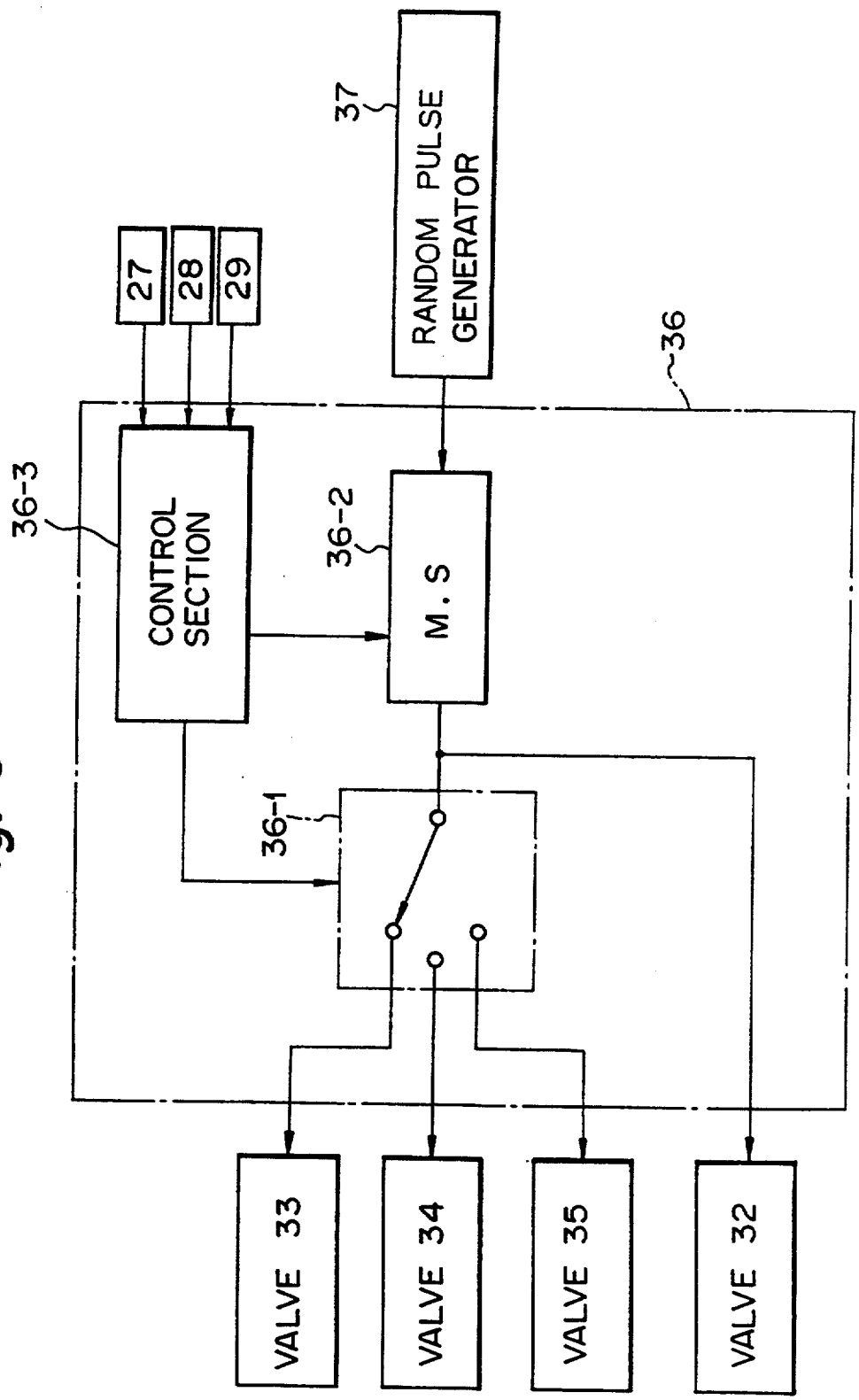
FIG. 6 is a diagrammatic view of the control circuit in FIG. 1.

FIG. 6 shows a schematic diagram of the control circuit 36 which includes a selector section 36-1, for selecting one of the valves 33 to 35, a mono-stable section 36-2 connected to the random pulse generator 37, and a control section 36-3 connected to the switches 27 to 29. The control section 36-3 operates one of the valves 33 to 35, which corresponds to one of the switches 27 to 29. The mono-stable section 36-3 issue a pulse every time a random signal is issued from the generator 37, so that a selected combination of the valve 32 and a valve from the valves 33 to 35 is operated.

Figure 7:
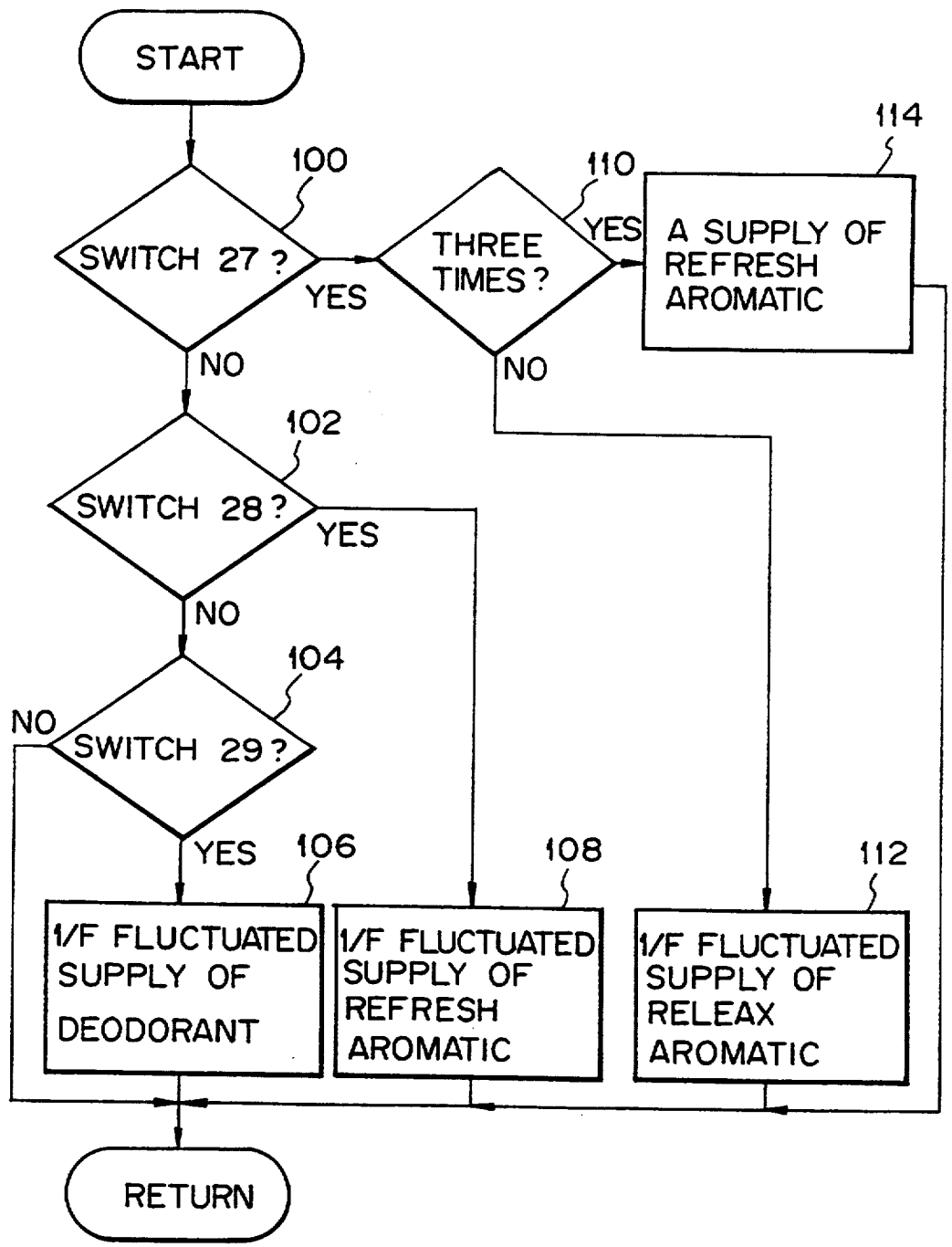
FIG. 7 is a flow chart illustrating the perfume control operation in the first embodiment.

Now, an operation of a first embodiment of the present invention will be described with reference to a flowchart in FIG. 7, which generally illustrates how the control circuit 36 in FIG. 1 operates.

At step 100, it is determined if the relaxing type aromatic selection switch 27 is ON. At step 102, it is determined if the refresh type aromatic selection switch 28 is ON. At step 104, it is determined if the deodorant selection switch 29 is ON. When the deodorant switch 29 is ON, the routine goes to step 106, where, in accordance with the random pulses generated by the generator 37, the control circuit 36 issues signals for randomly and pulsatively operating the electromagnetic valves 32 and 35, which allows the deodorant from the cassette 26 is supplied to the duct 16 and to be discharged from a selected outlet into the cabin.

When the refresh switch 28 is ON, the routine goes to step 108, where, in accordance with the random numbers generated by the generator 37, the control circuit 36 issues signals for randomly and pulsatively operating the electromagnetic valves 32 and 34 which allow the refreshing aromatic from the cassette 25 is supplied to the duct 16 and to be discharged from a selected outlet 10 into the cabin.

When the relaxing aromatic selection switch 27 is made ON, the routine goes to step 110, where it is determined if a random and intermittent supply of the relaxing type aromatic agent for a number of predetermined times (for example, three times) has been done. When it is determined that a random and intermittent supply of the relax type aromatic agent, for the predetermined number of times has not yet been done, the routine goes to step 112, where, in accordance with the random numbers generated by the generator 37, the control circuit 36 issues signals for randomly and pulsatively operating the electromagnetic valves 32 and 33, which allows the relaxing aromatic from the cassette 24 to be supplied to the duct 16 and to be discharged from a selected outlet into the cabin. When it determined that a random and pulsative supply of the relaxing type aromatic agent, for a predetermined number of times (for example, three times) has been done, the routine goes to step 114, where the valves 32 and 34 are opened to give a one-shot supply of the refreshing type aromatic agent from the cassette into the cabin via the duct 16. In other words, after the pulsative supply of the relaxing type aromatic agent for three times as shown in FIG. 8-(a), a one-shot supply of the refreshing type aromatic agent as shown in FIG. 8-(b) is done, which process is repeated.

Such an alternating supply of the relaxing type aromatic and the refreshing type aromatic is advantageous for obtaining an increased level of consciousness, which is advantageous from the view point of a safety during a driving, since a driver is prevented from losing concentration, while providing a desired aromatic condition in the cabin. Contrary to this, if only the relaxing type aromatic agent were supplied, the level of consciousness of a driver may be reduced, which may cause the driver to lose his or her concentration.

In the above first embodiment, a one-shot supply of the refreshing type aromatic is done after supply of the relaxing type aromatic. However, it may be possible to obtain a random, pulsative supply of the refresh type aromatic agent for more than two times.

Figure 9:
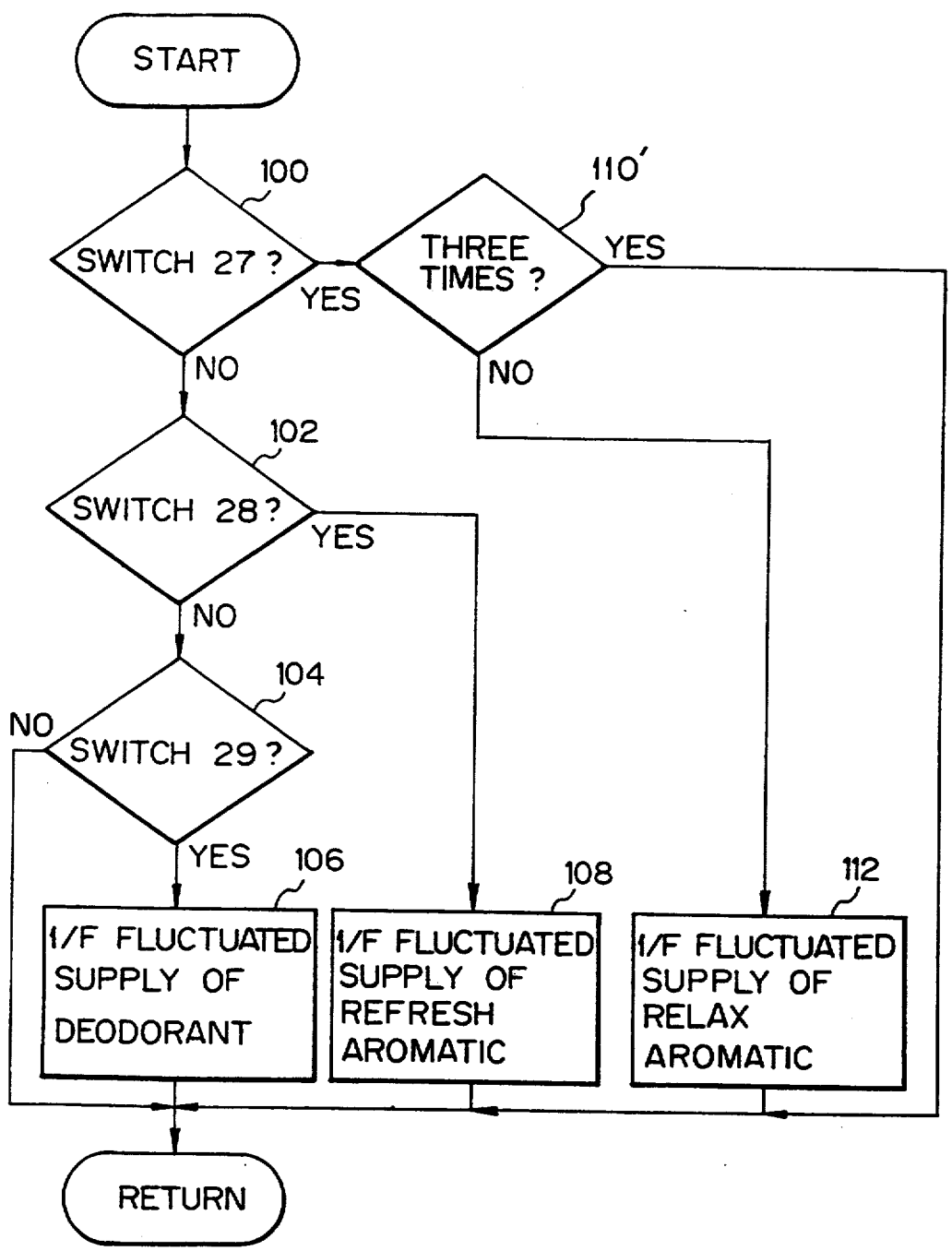
FIG. 9 is a flow chart illustrating the perfume control operation in the second embodiment.

FIG. 9 shows is a flowchart which is modified from FIG. 6 in that the step 114 is eliminated. At a result, an operation is obtained that, upon the selection of the relaxing type aromatic, for every supply of the relaxing type aromatic for a predetermined number of times, for example three times, the supply of any aromatic is stopped as shown in FIG. 10. Namely, in FIG. 9, the same routines as those in are performed FIG. 6 when the refreshing type aromatic selection switch 28 or the deodorant selection switch 29 is ON. Thus, a detailed explanation thereof is omitted while using the same reference numeral to blocks executing similar functions.

When the relaxing aromatic selection switch 27 is ON, the routine goes to step 110', where it is determined if a random and intermittent supply of the relaxing type aromatic agent for a predetermined number of times (for example, three times) has been done. When a no result is obtained at the step 110', the routing goes to step 112 where the 1/f fluctuation control, as explained for FIG. 6, is executed, so that, in accordance with the random pulses generated by the generator 37, the control circuit 36 issues signals for randomly and pulsatively operating the electromagnetic valves 32 and 33, which allows the relax aromatic from the cassette 24 to be supplied to the duct 16 and to be discharged from a selected outlet into the cabin. When it determined that a random and intermittent supply of the relaxing type aromatic agent for a predetermined number of times (for example, three times) has been done at step 110', nothing is done and the routine returns to the main routine. Thus, any supply of the relaxing aromatic agent is canceled at this timing t as shown in FIG. 10. Due to such an stoppage of the supply of the relaxing type aromatic agent after the execution of the supply of the aromatic for three times, a level of consciousness is prevented from being excessively reduced, which prevents the driver losing his or her concentration.

It should be noted that the first and second embodiments in FIGS. 6 and 9 can be applied to various air conditioning apparatus, other than for an automobile, such as in a factory where safety is strongly required. Furthermore, the aroma generating unit 1 can be independently used without combining it with any air conditioning system.

Figure 11:
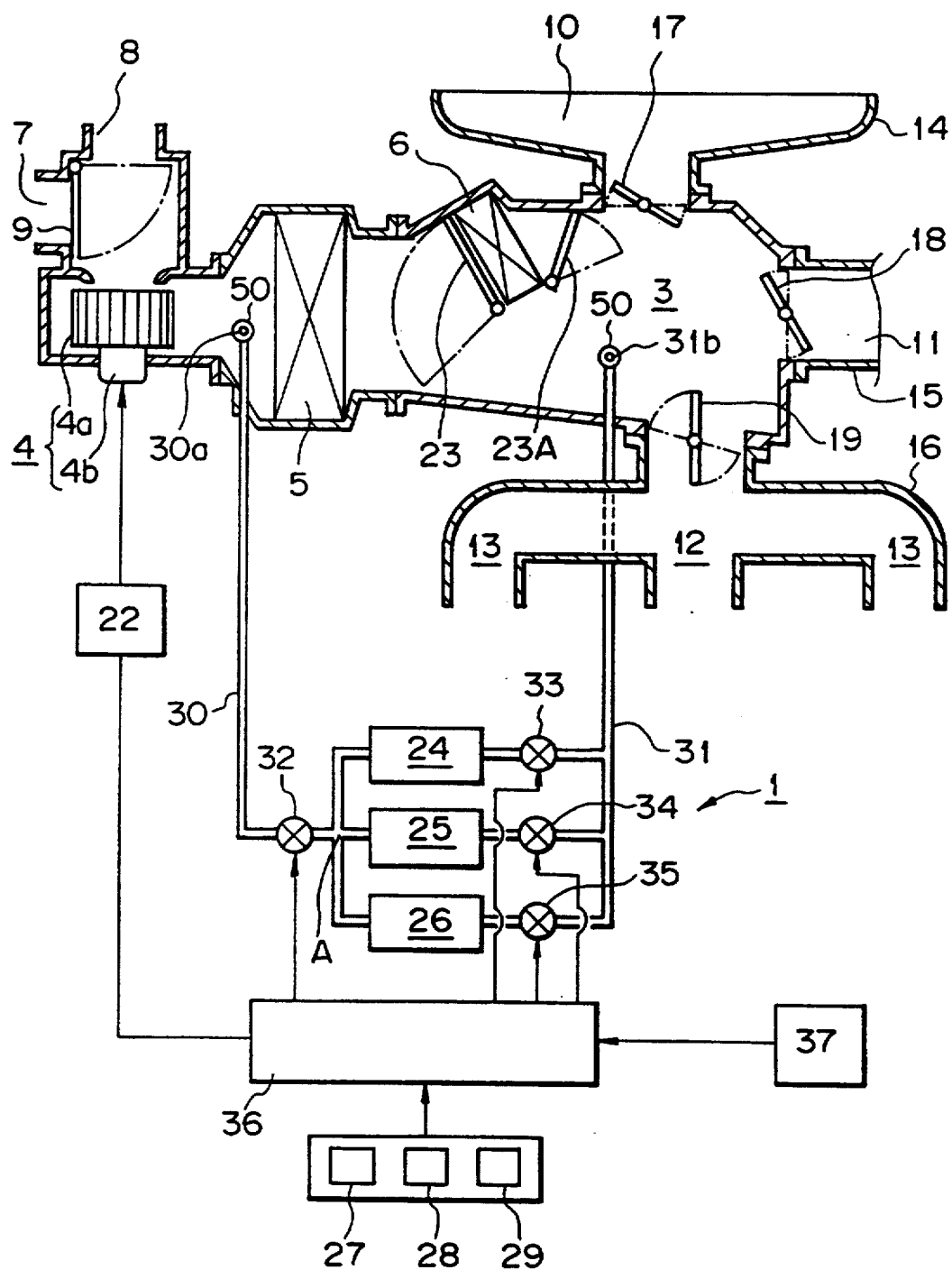
FIG. 11 is similar to FIG. 1, but illustrates the second embodiment.

FIG. 11 shows another modification, which is different from the construction in FIG. 1, in which the downstream end 31b of the downstream pipe 31 is connected to the duct 3 at a location downstream from the second air mix damper 23A located at the outlet of the heater core 6 and upstream from the dampers 17 to 19.

The arrangement of the downstream end 31b at a location downstream from the heater core 6 can prevent the introduced aromatic agents from being absorbed by the heater core 6 and prevent a reduction of the amount of the aromatic introduced into the cabin. Furthermore, the arrangement of the downstream end 33b at a location upstream from the dampers 17 to 19 is advantageous in that the aromatic agents can be introduced into the cabin at any modes including the upper outlet (foot) mode where the valve 19 at the upper outlet duct 16 is in the closed condition.

In the lower outlet mode, where the damper 19 to the upper outlet duct (face outlet duct) 16 is closed, a situation may arise that aroma as felt by the passenger to be relatively reduced due to the distance from the device 1 to the nose of the passenger. Thus, in order to obviate this problem, the duration of the opening of the valves during each pulsative opening thereof, which allows an increased amount of the aromatic agents to be supplied to the cabin is increased, thereby compensating for the increased distance, thereby maintaining the desired aromatic condition in the cabin during the lower (foot) outlet mode.

We claim:

1. A perfume generating device comprising:
   (a) a first container for storing a volatile, relaxing-type aromatic agent capable of giving a relaxing effect to reduce the level of consciousness;
   (b) a second container for storing a volatile, refreshing-type aromatic agent capable of giving a refreshing effect for increasing the level of consciousness;

(c) first means, responsive to an electric signal, for selectively opening the first container;

(d) second means, responsive to an electric signal, for selectively opening the second container;

(e) means for issuing an instruction for commencing a supply of the aromatic agents, and;

(f) means for issuing electric signals supplied to the first and second means for obtaining repetitions of cycles of a supply of the relaxing-type aromatic agent for a first predetermined period which is followed by a supply of the refreshing type aromatic agent for a second predetermined period when instructed.

2. A device according to claim 1, wherein the supply of the relaxing aromatic agent is done in a pulsative manner, and the frequency of the pulsative supply is such that the power spectrum is inversely proportional to the frequency.

3. A device according to claim 1, wherein said repetition means comprises a first means for obtaining a pulsative supply of the relaxing type aromatic agent for a predetermined number of times, a second means for obtaining at least one pulsative supply of the refreshing type aromatic agent, which is followed by a supply of the relaxing type aromatic, and means for obtaining an alternate operation between the first and second means.

4. A perfume generating device comprising:

(a) a container for storing a volatile, relaxing-type aromatic agent capable of giving a relaxing effect;

(b) first means, responsive to an electric signal, for selectively opening said container;

(c) means for issuing an instruction for commencing the supply of the aromatic agents, and;

(d) means for issuing electric signals supplied to the container opening means for obtaining a repetition of the supply of the relaxing type aromatic agent for a first predetermined period, which is followed by a stoppage of supply of the relaxing type aromatic agent for a second predetermined period.

5. A device according to claim 4, wherein the supply of the relaxing aromatic agent is done pulsatively, and the frequency of the pulsative supply is such that the power spectrum is inversely proportional to the frequency.

6. An air conditioning apparatus for a vehicle, comprising:

(a) a duct having an upstream end for introduction of air and a downstream end having at least one opening opening into the cabin, and a damper for controlling the opening;

(b) means for creating a flow of air in the duct;

(c) heat exchanging means for obtaining a heat exchange between the air in the duct and a heat exchanging medium;

(d) a first container for storing a volatile, relaxing-type aromatic agent capable of giving a relaxing effect;

(e) a second container for storing a volatile, refreshing type aromatic agent capable of giving a refreshing effect;

(f) a passageway on which the first and second container are arranged in parallel, and which has an upstream end connected to the duct as a location downstream from the flow creating means and a downstream end connected to said duct at a location downstream from the heat exchanging means;

(g) first means, responsive to an electric signal, for selectively opening the first container;

(h) second means, responsive to an electric signal, for selectively opening the second container;

(i) means for issuing an instruction for supplying the aromatic agents to the cabin of the vehicle, and;

(j) means for issuing signals to the first and second means for obtaining repetitions of cycles of supplying of the relaxing type aromatic agent to the cabin for a first predetermined period, which is followed by supplying the refreshing-type aromatic agent for a predetermined second period.

7. An air-conditioning apparatus, according to claim 6, for an automobile having a water-cooled internal-combustion engine, wherein said heat exchanging means comprises an evaporator located in a refrigerating cycle, and a heater core arranged in a cooling water recirculating circuit of said engine, and;

wherein the downstream end of the passageway is connected to the air conditioning duct at a position between the heater core and the damper.

8. An air conditioning apparatus, according to claim 6, for an automobile having a water-cooled internal-combustion engine, wherein said heat exchanging means comprises an evaporator located in a refrigerating cycle, and a heater core arranged in a cooling-water recirculating-circuit of said engine;

wherein said opening of the duct is opened to the cabin at a vertical level for providing air flow directed to an upper part of a passenger, and;

wherein the downstream end of the passageway is connected to the air conditioning duct at a position downstream from the damper.

9. An air conditioning apparatus for a vehicle, comprising:

(a) a duct having an upstream end for introduction of air and a downstream end having at least one opening opened to the cabin, and a damper for controlling the opening;

(b) means for creating a flow of air in the duct;

(c) an air conditioning means for allowing the air flow to be contacted with a heat exchanging medium;

(d) a passageway which has an upstream end connected to the duct at a location downstream from the flow creating means and a downstream end connected to said duct at a location downstream from the air conditioning means;

(e) a container on the passageway for storing a volatile, relaxing-type aromatic agent capable of obtaining a relaxing effect;

(f) means, responsive to an electric signal, for selectively opening said container;

(g) means for issuing an instruction for commencing a supply of the aromatic agents to the cabin, and;

(h) means for issuing electric signals supplied to the container opening means for obtaining a repetition of cycles of a supply of the relaxing type aromatic agent for a first predetermined period, which are followed by a stoppage of supply of the relaxing type aromatic agent for a second predetermined period when instructed.

10. An air conditioning apparatus for a vehicle which includes a water-cooled internal-combustion engine, comprising:

(a) a duct having an upstream end for the introduction of air and a downstream end having at least one opening opening into the cabin, and a damper for controlling the opening;

(b) fan means for creating a flow of air in the duct;

(c) an evaporator for obtaining a heat exchange between the air and a refrigerating line;

(d) a heater core for obtaining a heat exchange between the air and hot water in a cooling water line of said engine;

(e) at least one container for storing a volatile aromatic agent;

(f) a passageway on which the container is arranged, and which has an upstream end connected to the duct at a location downstream from the fan and a downstream end connected to the air conditioning duct at a location between the heater core and the damper, and;

(g) controlling means for controlling the supply of the aromatic agent in the container to the air conditioning duct via said passageway.

11. An air conditioning apparatus according to claim 10, further comprising means for varying a setting of the duration of the supply of the aromatic agent.

12. An air-conditioning apparatus for a vehicle, comprising:

(a) a duct having an upstream end for the introduction of air and a downstream end having at least one opening opened to the cabin, and a damper for controlling the opening;

(b) fan means for creating a flow of air in the duct;

(c) air conditioning means for controlling the temperature of the air in the duct;

(d) at least one container for storing a volatile aromatic agent;

(f) a passageway on which the container is arranged, and which has an upstream end connected to the duct at a location downstream from the fan and a downstream end connected to the air conditioning duct at a location downstream from the air conditioning means, and;

(g) controlling means for controlling the supply of the aromatic agent in the container to the air conditioning duct via said passageway, at each of the end of the passageway for connection with the duct, a pipe fitting being provided, which has a first end of tubular shape connected to a flexible tube constructing the passageway, and a second tubular end connected to the air conditioning duct, the first tubular portion having, at its end adjacent the second tubular portion, a flange portion which is face to face contact with a wall of the duct, the second end having a plurality of radial extending, circumferentially spaced fingers which are tapered away from the flange portion, so that an annular groove is created between the flange portion and the finger portion, to which the wall portion is snap fitted.

* * * * *